United States Patent [19]

Katz

[11] 4,423,246

[45] Dec. 27, 1983

[54] SELECTED TRICHLOROACETAMIDINES

[75] Inventor: Lawrence E. Katz, Orange, Conn.

[73] Assignee: Olin Corporation, New Haven, Conn.

[21] Appl. No.: 350,912

[22] Filed: Feb. 22, 1982

[51] Int. Cl.$^3$ .................. C07C 123/00; C07C 103/32; C07C 145/02
[52] U.S. Cl. .................................. 564/102; 564/209; 564/225
[58] Field of Search ....................... 564/225, 102, 209; 424/326

[56] References Cited

FOREIGN PATENT DOCUMENTS 2601137  7/1976  Fed. Rep. of Germany ...... 564/225
1490671  11/1977  United Kingdom .

Primary Examiner—Natalie Trousof
Assistant Examiner—L. Hendriksen
Attorney, Agent, or Firm—William D. Sabo

[57] ABSTRACT

Disclosed are selected trichloroacetamidines having the formula

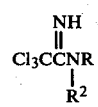

wherein
R is selected from the group consisting of

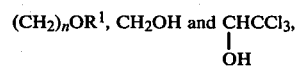

wherein n is 2, 3 or 4 and $R^1$ is a lower alkyl group having 1 to 4 carbon atoms; and
$R^2$ is selected from the group consisting of H, SCCl$_3$ and COCCl$_3$.

These compounds are disclosed to be agricultural fungicides.

3 Claims, No Drawings

SELECTED TRICHLOROACETAMIDINES

BACKGROUND OF THE INVENTION

1. Field of the Invention

This invention relates to selected trichloroacetamidines and their use as fungicides.

2. Description of the Prior Art

British Pat. No. 1,490,671 discloses certain perhaloalkylamidines and their use as cardiotonic agents.

BRIEF SUMMARY OF THE INVENTION

Accordingly, the present invention is directed to, as compositions of matter, selected trichloroacetamidines having the formula

  (I)

wherein
R is selected from the group consisting of (CH$_2$)$_n$OR$^1$, CH$_2$OH and CHCCl$_3$,
                                      |
                                      OH wherein n is 2, 3 or 4 and R$^1$ is a lower alkyl group having 1 to 4 carbon atoms; and
R$^2$ is selected from the group consisting of H, SCCl$_3$ and COCCl$_3$.

The present invention is also directed to the use of these compounds as agricultural fungicides.

DETAILED DESCRIPTION

The trichloroacetamidine compounds of the present invention may be prepared from trichloroacetonitrile or some of its derivatives. These general reactions are illustrated below in equations (A), (B) and (C). In equation (A), trichloroacetonitrile is reacted with 2-ethoxyethylamine to form N-(2-ethoxyethyl)trichloroacetamidine. In equation (B), trichloroacetamidine is reacted with formaldehyde to produce trichloroacetamidinomethanol.

Cl$_3$CC≡N + H$_2$NCH$_2$CH$_2$OCH$_2$CH$_3$ ⟶  (A)

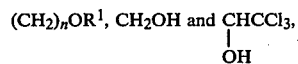

  (B)

These trichloroacetamidine products may be then reacted with perchloromethyl mercaptan or trichloroacetylchloride to form derivative compounds of the present invention. For example, in equation (C), N-(2-ethoxyethyl)trichloroacetamidine is reacted with trichloroacetylchloride to form N-trichloroacetyl-N-(2-ethoxyethyl)trichloroacetamidine.

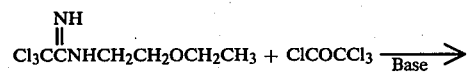 + ClCOCCl$_3$ $\xrightarrow{\text{Base}}$ (C)

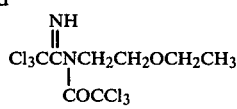

Trichloroacetonitrile is a commercially available material. The trichloroacetamidine reactant is made by reacting trichloroacetonitrile with ammonia. See German Pat. No. 671,785.

The compounds which are reacted with trichloroacetonitrile are alkoxyalkylamines. These compounds may be made by reacting the corresponding chloroether with ammonia. See Hickenbottom, W. J., Reactions of Organic Compounds (3rd Edition), pages 527 and 528 (1957). For example, 4-methoxy-1-chlorobutane may be reacted with ammonia to form 4-methoxybutylamine. Various alkoxyalkylamines such as 3-ethoxypropylamine, 3-methoxypropylamine and 2-ethoxyethylamine are commercially available.

The formaldehyde and chloral reactants are commercially available. Likewise, perchloromethyl mercaptan and trichloroacetylchloride are commercially available.

A wide variety of conventional reaction conditions may be employed in the synthesis of the present compounds according to equations (A), (B) and (C), and the present invention is not intended to be limited to any particular reaction conditions. For example, the reactions illustrated by equation (A) may be performed by using at least a molar amount of the compound which is reacted with trichloroacetonitrile (e.g. from about 0.0 to about 1.0 molar excess). Although a solvent is not generally necessary, any suitable inert solvent may be employed. Alternatively, however, it is preferred to utilize an excess of trichloroacetonitrile to serve as the solvent medium. The reaction temperature and time will both depend upon many factors. For example, when the reaction is carried out in the absence of solvent, a reaction temperature from about 0° C. to about 35° C. and a reaction time from about 2 hours to about 18 hours are preferred. When a solvent is employed, a reaction temperature from about 20° C. to about 120° C. and a reaction time from about 2 hours to about 18 hours are preferred.

Advantageously and preferably, the reactions illustrated by equation (B) are performed with at least a molar amount of the compound which is reacted with trichloroacetamidine (e.g. from about 0.0 to about 1.0 molar excess). Any of a number of inert solvents may be used, although water is preferred. Reaction temperatures preferably range from about 20° C. to about 120° C. and reaction times preferably range from about 2 hours to about 18 hours.

Advantageously and preferably, the reactions illustrated by equation (C) are performed with at least a molar amount of the compound which is reacted with the trichloroacetamidine product of the reactions shown by equation (A) or equation (B) (e.g. from about 0.0 to about 1.0 molar excess). It is also preferred to carry out the reaction in the presence of a base such as triethylamine or sodium bicarbonate. Alternatively, however, an excess of trichloroacetamidine may be used to conduct the reaction under basic conditions. Any suitable inert solvent, such as those mentioned above for use in carrying out the reactions shown by equation (A) may be employed. In most situations, reaction temperatures from about 20° C. to about 120° C.

and reaction times from about 1 hour to about 8 hours are preferred.

The desired product may be recovered from the reaction mixture by any conventional means, for example, distillation, recrystallization, precipitation, and the like. Finally, it should be noted that while the reactions illustrated by equations (A), (B) and (C) are preferred, other synthesis methods for preparing compounds of the present invention may also be employed.

Representative compounds of the present invention include the following:

N-(2-ethoxyethyl)trichloroacetamidine;
N-(3-ethoxypropyl)trichloroacetamidine;
N-(3-methoxypropyl)trichloroacetamidine;
N-(3-methoxybutyl)trichloroacetamidine;
N-trichloromethylthio-N-(2-ethoxyethyl)trichloroacetamidine;
N-trichloroacetyl-N-(2-ethoxyethyl)trichloroacetamidine;
trichloroacetamidinomethanol; and
1-trichloroacetamidino-2,2,2-trichloroethanol.

Also, in accordance with the present invention, it has been found that the compounds of Formula (I) above may be utilized as effective foliar or soil fungicides. In practicing the process of the present invention, fungi are contacted with a fungicidally effective amount of one or more of these compounds. It is to be understood that the term "fungicidally effective amount" as used in the specification and claims herein is intended to include any amount that will kill or control said foliar or soil fungi when either employed by itself (i.e., in full concentration) or in sufficient concentrations within a carrier or other substance. Of course, this amount may be constantly changing because of the possible variations in many parameters. Some of these may include: the number and type of fungi to be controlled or killed; the type of media to which the present compound can be applied (e.g., plants or soil); the degree of effectiveness required; and the type of carrier, if any. Generally speaking, applications of an aqueous solution containing at least about 3.2, more preferably in the range of about 3.2 to about 50, pounds per acre of the chemical of the present invention may give satisfactory fungi control.

This step of contacting may be accomplished by applying this compound to the fungi themselves, their habitat, or dietary media such as vegetation, crops and the like, including many which these pests may attack.

The above-mentioned compounds of the present invention may be formulated and applied by any conventional methods that include using the compounds alone or with a carrier of other substances which may enhance the effectiveness of the chemical or facilitate handling. Moreover, the activity of the present compounds may be broadened by the addition thereto of other known pesticides such as other fungicides, herbicides, insecticides, and the like.

Specific methods of formulating and applying these active compounds include applying them in the form of dusts, dust or emulsion concentrates, wettable powders and concentrates, granulates, dispersions, sprays, solutions, and the like.

The dusts are usually prepared by simply grinding together from about 1% to about 15% by weight of the active compound with a finely divided inert diluent such as walnut flour, diatomaceous earth, fullers earth, attaclay, talc, or kaolin. Dust concentrates are made in similar fashion except that about 16% to about 75% by weight of active compound is ground usually together with the diluent. In practice, dust concentrates are then generally admixed at the site of use with more inert diluent before being applied to the plant foliage, soil or animals which are to be protected from fungi attack.

Wettable powders are generally prepared in the same manner as dust concentrates, but usually about 1% to about 10% by weight of a dispersing agent, for example, an alkali metal lignosulfonate, and about 1% to about 10% of a surfactant, such as a non-ionic surfactant, are incorporated in the formulation. For application to agronomic crops, shrubs, ornamentals, and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic or aromatic hydrocarbon or their derivatives. It is preferred that the solvent be odorless and, moreover, be inert to the active compound.

It should be clearly understood that the fungicide formulations, the ingredients which may make up such formulations other than the active compound, the dosages of these ingredients, and means of applying these formulations may include all known and conventional substances, amounts, and means, respectively, that are suitable for obtaining the desired fungicidal result. And, therefore, such process parameters are not critical to the present invention.

Fungicides of the present invention may be effective for the control of broad classes of foliar and soil fungi. A specific illustration of foliar fungi wherein fungicidal activity has been shown is cucumber anthracnose. A specific illustration of soil fungi wherein fungicidal activity has been shown is pythium.

The following examples further illustrate the present invention. All parts and percentages employed therein are by weight unless otherwise indicated. Yields given are percent molar yields.

EXAMPLE 1

Preparation of N-(2-Ethoxyethyl)Trichloroacetamidine

To 15 ml (0.5 mole) trichloroacetonitrile in an ice bath, was added 8.9 g (0.10 mole) 2-ethoxyethylamine. The addition was carried out over 20 minutes and the reaction temperature rose to 35° C. After 20 minutes additional stirring at 0° C., it was stirred at room temperature overnight. The mixture was washed to give 12.0 g. Distillation yielded: (1) 9.1 g (B.P. 0.41 mm, 92°–97° C.); (2) 1.9 g (B.P. 0.41 mm, 96° C.). Total yield:

10.9 g (47%). The structure was confirmed via IR, VPC, and elemental analysis.

Analysis for $C_6H_{11}N_2Cl_3O$

|  | C | H | N | Cl |
|---|---|---|---|---|
| Calculated | 30.86 | 4.75 | 12.00 | 45.55 |
| Found | 30.55 | 4.63 | 12.02 | 45.76 |

EXAMPLE 2

Preparation of N-Trichloromethylthio-N-(2-Ethoxyethyl)Trichloroacetamidine

To 4.7 g (0.02 mole) N-(2-ethoxyethyl)trichloroacetamidine, 2.1 g (0.02 mole) triethylamine, and 50 ml ether, cooled in an ice bath, was added 3.8 g (0.02 mole) perchloromethylmercaptan over 15 minutes. The temperature rose from 1.5° C. to 8.5° C. The solution was stirred 1¼ hours longer, filtered and rotary evaporated to give 6.4 g solid. Recrystallization from petroleum ether (cooling in dry ice) gave 4.0 g (54% yield; mp 65°–66° C.). The structure was confirmed via IR and elemental analysis.

Analysis for $C_7H_{10}N_2Cl_6SO$

|  | C | H | N | Cl | S |
|---|---|---|---|---|---|
| Calculated | 21.95 | 2.63 | 7.32 | 55.55 | 8.37 |
| Found | 21.52 | 2.71 | 7.11 | 54.91 | 7.99 |

EXAMPLE 3

Preparation of N-Trichloroacetyl-N-(2-Ethoxyethyl)Trichloroacetamidine

To 4.7 g (0.02 mole) N-(2-ethoxyethyl)trichloroacetamidine, 2.1 g (0.02 mole) triethylamine, and 50 ml ether, was added 3.7 g (0.02 mole) trichloroacetylchloride. The reaction temperature rose from 22° C. to 32° C. and the solution was stirred 1¼ hours after the addition. The precipitate was removed by filtration and the filtrate rotary evaporated to give 7.9 g residue. Recrystallization from petroleum ether gave (after cooling with dry ice) 4.1 g (58% yield; mp 57°–60° C.). The structure was confirmed via IR and elemental analysis.

Analysis for $C_8H_{10}N_2Cl_6O_2$

|  | C | H | N | Cl |
|---|---|---|---|---|
| Calculated | 25.75 | 2.65 | 7.36 | 55.85 |
| Found | 25.69 | 2.82 | 7.51 | 55.61 |

EXAMPLE 4

Preparation of Trichloroacetamidinomethanol

To 4.0 g (0.024 mole) trichloroacetamidine in 30 ml water was added 2 ml (0.025 mole) 37% formaldehyde solution. The temperature rose from 27° C. to 35° C. and a white solid precipitated. After stirring overnight, the product was filtered, washed, and dried to give 1.5 g (33% yield; mp 109° C.). The structure was confirmed via IR and elemental analysis.

Analysis for $C_3H_5N_2Cl_3O$

|  | C | H | N | Cl |
|---|---|---|---|---|
| Calculated | 18.82 | 2.63 | 14.63 | 55.56 |
| Found | 19.08 | 2.23 | 15.09 | 54.91 |

EXAMPLE 5

Preparation of 1-Trichloroacetamidino-2,2,2-Trichloroethanol

To 4.0 g (0.024 mole) trichloroacetamidine in 50 ml water was added 3.7 g (0.025 mole) chloral. The temperature rose from 28°–36.5° C. and a white precipitate came out of solution. The mixture was stirred overnight, filtered, and the solid dried to give 3.1 g (50% yield; mp 105°–107° C.). The structure was confirmed via IR, NMR, and elemental analysis.

Analysis for $C_4H_4N_2Cl_6O$

|  | C | H | N | Cl |
|---|---|---|---|---|
| Calculated | 15.56 | 1.31 | 9.07 | 68.89 |
| Found | 15.51 | 1.49 | 9.12 | 68.36 |

Foliar Fungicide Screen

The active materials formed in Examples 1–5 were tested for activity as effective fungicides.

A uniform aqueous dispersion of each chemical made in the above examples was first prepared. These dispersions were made by dissolving each chemical in a solution of acetone containing the surfactant TRITON X-155[1] (concentration 500 parts per million). Next, this solution was diluted with water (1:9) to obtain a stock solution of 10% by volume acetone and 90% by volume water with 50 parts per million TRITON X-155 and the test chemical contained therein. This stock solution was diluted further with water/acetone mix to provide the desired concentration of the test material, if required.

[1] A polyether alcohol manufactured by Rohm and Haas, Philadelphia, Pennsylvania.

The aqueous solutions containing each chemical were applied to various plants according to the methods stated below. These tests were designed to evaluate the ability of the chemical to protect non-infected foliage and eradicate recently established infection against major types of fungi such as anthracnose that attack above-ground parts of plants.

Cucumber Anthracnose

Two week old cucumber plants were sprayed while rotating the plants on a turntable with an aqueous solution that contained 260 parts per million by weight of the active chemicals of Examples 1–5. Simultaneously, the soil in each pot was drenched with an aqueous dispersion of each chemical in the amount of 25 lb/acre. After the spray deposit had dried, the plants were atomized with a suspension of cucumber anthracnose spores (*Collectotrichum lagenarium*) and placed in a moist chamber at 70° F. for 24 hours. After 5 days, the severity of pustule formation was rated on a scale of 0 (no inhibition) to 10 (complete inhibition). Subsequent tests were conducted as described except the materials were tested for control at lower dosages. See Table I for the results of these tests.

TABLE I
FUNGICIDAL ACTIVITY AGAINST CUCUMBER ANTHRACNOSE

| Compound | 25 lb/acre drench & 260 ppm spray | 12.5 lb/acre drench | 6.3 lb/acre drench | 3.2 lb/acre drench |
|---|---|---|---|---|
| Example 1 | 5 | — | — | — |
| Example 2 | 2 | — | — | — |
| Example 3 | 5 | — | — | — |
| Example 4 | 8 | 7 | 1 | 5 |
| Example 5 | 6 | — | — | — |

Soil Fungicide Disinfectant Screen

Pythium ultimum was cultured on a sterile medium of corn meal and number 4 Zonolite in petri dishes. The culture was then blended with sterile soil. Ten pea seeds were pressed into the infested soil and covered with additional infested soil. Four controls were seeded: uninoculated, inoculated, chemical in uninoculated soil and standard chemical in inoculated soil. A mixture of the test material at 1040 parts per million was added to each cup at a rate of 10 ml (25 lb/acre). The cups were held in closed plastic containers for 3 days before opening. Records were made of the emergence of seedlings and freedom of the hypocotyl from brown lesions after 11 additional days in the open. The chemicals were rated depending upon the percentage of emergence and severity of lesions on survivors from 0 (severe infection on all plants) to 10 (no lesions). Subsequent tests were conducted as described except the materials were tested for control at lower dosages. See Table II for the results of these tests.

TABLE II
FUNGICIDAL ACTIVITY AGAINST PYTHIUM

| Compound | 25 lb/acre | 12.5 lb/acre | 6.3 lb/acre | 3.2 lb/acre |
|---|---|---|---|---|
| Example 1 | 6 | 9 | 8.5 | 4 |
| Example 2 | 8 | 6 | 0 | — |
| Example 4 | 8 | 7 | 0 | — |
| Example 5 | 7 | 6 | 0 | — |

What is claimed is:

1. A compound having the formula:

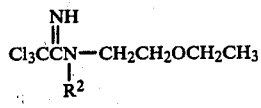

wherein $R^2$ is selected from the group consisting of $SCCl_3$ and $COCCl_3$.

2. A compound having the formula:

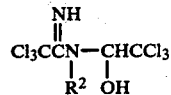

wherein $R^2$ is selected from the group consisting of H, $SCCl_3$ and $COCCl_3$.

3. The compound of claim 2 wherein said compound is 1-trichloroacetamidino-2,2,2-trichloroethanol.

* * * * *